United States Patent
Dickhans

(10) Patent No.: US 11,974,805 B2
(45) Date of Patent: May 7, 2024

(54) MICROWAVE ABLATION SYSTEM

(71) Applicant: Covidien LP, Mansfield, MA (US)

(72) Inventor: William J. Dickhans, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1029 days.

(21) Appl. No.: 16/853,925

(22) Filed: Apr. 21, 2020

(65) Prior Publication Data

US 2020/0246071 A1    Aug. 6, 2020

Related U.S. Application Data

(63) Continuation of application No. 14/828,682, filed on Aug. 18, 2015, now Pat. No. 10,624,697.

(Continued)

(51) Int. Cl.
*A61B 18/18*       (2006.01)
*A61B 90/00*       (2016.01)
(Continued)

(52) U.S. Cl.
CPC .......... *A61B 18/1815* (2013.01); *A61B 90/39* (2016.02); *A61B 2018/00017* (2013.01); *A61B 2018/00023* (2013.01); *A61B 2018/00029* (2013.01); *A61B 2018/00511* (2013.01); *A61B 2018/00541* (2013.01);
(Continued)

(58) Field of Classification Search
CPC ........ A61B 18/1815; A61B 2018/1861; A61B 2018/1869
See application file for complete search history.

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CN | 1103807 C | 3/2003 |
| DE | 390937 C | 3/1924 |

(Continued)

OTHER PUBLICATIONS

Extended European Search Report issued in corresponding Application No. EP 20175891.9 dated Sep. 22, 2020 (9 pages).

(Continued)

*Primary Examiner* — Jaymi E Della
(74) *Attorney, Agent, or Firm* — Carter, DeLuca & Farrell LLP

(57) ABSTRACT

A microwave ablation catheter assembly is provided. A coaxial cable configured to connect to a microwave energy source at its proximal end and at its distal end to a distal radiating section. The coaxial cable includes inner and outer conductors and a dielectric positioned therebetween. An extended working channel is configured to receive the coaxial cable for positioning the coaxial cable adjacent target tissue. At least a portion of an inner surface of the extended working channel is electrically conductive. The electrically conductive inner surface of the extended working channel may function as a balun to maintain a balanced signal between the inner and outer conductors of the coaxial cable when the distal radiating section of the coaxial cable is energized.

20 Claims, 5 Drawing Sheets

Related U.S. Application Data

(60) Provisional application No. 62/041,773, filed on Aug. 26, 2014.

(51) Int. Cl.
*A61B 18/00* (2006.01)
*A61B 34/10* (2016.01)
*A61B 34/20* (2016.01)

(52) U.S. Cl.
CPC .............. *A61B 2018/00577* (2013.01); *A61B 2018/1861* (2013.01); *A61B 2034/107* (2016.02); *A61B 2034/2051* (2016.02)

(56) References Cited

U.S. PATENT DOCUMENTS

| | | |
|---|---|---|
| D266,842 S | 11/1982 | Villers et al. |
| D278,306 S | 4/1985 | McIntosh |
| 4,583,589 A | 4/1986 | Kasevich |
| D295,893 S | 5/1988 | Sharkany et al. |
| D295,894 S | 5/1988 | Sharkany et al. |
| 4,846,171 A | 7/1989 | Kauphusman et al. |
| 4,896,671 A | 1/1990 | Cunningham et al. |
| 5,301,687 A | 4/1994 | Wong et al. |
| 5,342,357 A | 8/1994 | Nardella |
| 5,342,393 A | 8/1994 | Stack |
| 5,364,392 A | 11/1994 | Warner et al. |
| 5,370,644 A | 12/1994 | Langberg |
| D354,218 S | 1/1995 | Van de Peer |
| 5,413,571 A | 5/1995 | Katsaros et al. |
| 5,529,067 A | 6/1996 | Larsen et al. |
| 5,540,715 A | 7/1996 | Katsaros et al. |
| 5,545,137 A | 8/1996 | Rudie et al. |
| 5,582,617 A | 12/1996 | Klieman et al. |
| 5,603,697 A | 2/1997 | Grundy et al. |
| 5,624,392 A | 4/1997 | Saab |
| 5,630,833 A | 5/1997 | Katsaros et al. |
| 5,649,959 A | 7/1997 | Hannam et al. |
| 5,685,839 A | 11/1997 | Edwards et al. |
| 5,693,082 A | 12/1997 | Warner et al. |
| 5,741,249 A | 4/1998 | Moss et al. |
| 5,817,119 A | 10/1998 | Klieman et al. |
| 5,846,248 A | 12/1998 | Chu et al. |
| 5,974,343 A | 10/1999 | Brevard et al. |
| 5,980,505 A | 11/1999 | Wilson |
| 5,993,447 A | 11/1999 | Blewett et al. |
| 5,995,875 A | 11/1999 | Blewett et al. |
| 6,014,581 A | 1/2000 | Whayne et al. |
| D424,693 S | 5/2000 | Pruter |
| D424,694 S | 5/2000 | Tetzlaff et al. |
| D425,201 S | 5/2000 | Tetzlaff et al. |
| 6,061,551 A | 5/2000 | Sorrells et al. |
| 6,066,139 A | 5/2000 | Ryan et al. |
| 6,099,550 A | 8/2000 | Yoon |
| 6,106,524 A | 8/2000 | Eggers et al. |
| 6,117,101 A | 9/2000 | Diederich et al. |
| 6,139,527 A | 10/2000 | Laufer et al. |
| 6,186,978 B1 | 2/2001 | Samson et al. |
| 6,188,355 B1 | 2/2001 | Gilboa |
| 6,210,367 B1 | 4/2001 | Carr |
| 6,221,039 B1 | 4/2001 | Durgin et al. |
| 6,235,024 B1 | 5/2001 | Tu |
| 6,239,724 B1 | 5/2001 | Doron et al. |
| 6,277,113 B1 | 8/2001 | Berube |
| D449,886 S | 10/2001 | Tetzlaff et al. |
| 6,348,039 B1 | 2/2002 | Flachman |
| 6,352,503 B1 | 3/2002 | Matsui et al. |
| 6,355,016 B1 | 3/2002 | Bagaoisan et al. |
| D457,958 S | 5/2002 | Dycus et al. |
| D457,959 S | 5/2002 | Tetzlaff et al. |
| 6,398,781 B1 | 6/2002 | Goble et al. |
| 6,419,680 B1 | 7/2002 | Cosman et al. |
| 6,427,089 B1 | 7/2002 | Knowlton |
| 6,485,486 B1 | 11/2002 | Trembly et al. |
| 6,496,737 B2 | 12/2002 | Rudie et al. |
| 6,496,738 B2 | 12/2002 | Carr |
| 6,514,249 B1 | 2/2003 | Maguire et al. |
| 6,527,753 B2 | 3/2003 | Sekine et al. |
| 6,547,788 B1 | 4/2003 | Maguire et al. |
| 6,575,969 B1 | 6/2003 | Rittman, III et al. |
| 6,599,288 B2 | 7/2003 | Maguire et al. |
| 6,629,974 B2 | 10/2003 | Penny et al. |
| 6,635,055 B1 | 10/2003 | Cronin |
| 6,645,234 B2 | 11/2003 | Evans et al. |
| 6,652,515 B1 | 11/2003 | Maguire et al. |
| 6,676,657 B2 | 1/2004 | Wood |
| D487,039 S | 2/2004 | Webster et al. |
| 6,689,127 B1 | 2/2004 | Gough et al. |
| 6,706,040 B2 | 3/2004 | Mahon et al. |
| 6,723,091 B2 | 4/2004 | Goble et al. |
| 6,740,108 B1 | 5/2004 | Just et al. |
| 6,770,070 B1 | 8/2004 | Balbierz |
| 6,773,409 B2 | 8/2004 | Truckai et al. |
| 6,780,183 B2 | 8/2004 | Jimenez, Jr. et al. |
| 6,786,905 B2 | 9/2004 | Swanson et al. |
| D496,997 S | 10/2004 | Dycus et al. |
| D499,181 S | 11/2004 | Dycus et al. |
| 6,847,848 B2 | 1/2005 | Sterzer et al. |
| 6,869,431 B2 | 3/2005 | Maguire et al. |
| 6,893,436 B2 | 5/2005 | Woodard et al. |
| 6,898,454 B2 | 5/2005 | Atalar et al. |
| 6,932,776 B2 | 8/2005 | Carr |
| 6,997,925 B2 | 2/2006 | Maguire et al. |
| 7,004,938 B2 | 2/2006 | Ormsby et al. |
| 7,047,063 B2 | 5/2006 | Burbank et al. |
| 7,047,068 B2 | 5/2006 | Haissaguerre |
| 7,049,068 B2 | 5/2006 | Thorp et al. |
| D525,361 S | 7/2006 | Hushka |
| 7,089,063 B2 | 8/2006 | Lesh et al. |
| 7,113,832 B2 | 9/2006 | Longo |
| D531,311 S | 10/2006 | Guerra et al. |
| D533,942 S | 12/2006 | Kerr et al. |
| D535,027 S | 1/2007 | James et al. |
| 7,179,255 B2 | 2/2007 | Lettice et al. |
| 7,197,356 B2 | 3/2007 | Carr |
| D541,418 S | 4/2007 | Schechter et al. |
| 7,200,445 B1 | 4/2007 | Dalbec et al. |
| D541,938 S | 5/2007 | Kerr et al. |
| 7,226,446 B1 | 6/2007 | Mody et al. |
| 7,233,820 B2 | 6/2007 | Gilboa |
| 7,261,001 B2 | 8/2007 | Heijnsdijk et al. |
| 7,263,398 B2 | 8/2007 | Carr |
| 7,275,547 B2 | 10/2007 | Willis |
| 7,285,116 B2 | 10/2007 | de la Rama et al. |
| 7,294,125 B2 | 11/2007 | Phalen et al. |
| 7,294,127 B2 | 11/2007 | Leung et al. |
| 7,300,436 B2 | 11/2007 | Penny et al. |
| 7,303,558 B2 | 12/2007 | Swanson |
| 7,318,823 B2 | 1/2008 | Sharps et al. |
| D564,662 S | 3/2008 | Moses et al. |
| 7,387,626 B2 | 6/2008 | Edwards et al. |
| 7,402,168 B2 | 7/2008 | Sanderson et al. |
| 7,410,486 B2 | 8/2008 | Fuimaono et al. |
| D576,932 S | 9/2008 | Strehler |
| 7,438,712 B2 | 10/2008 | Chouinard |
| 7,460,898 B2 | 12/2008 | Brister et al. |
| 7,467,015 B2 | 12/2008 | van der Weide |
| 7,507,229 B2 | 3/2009 | Hewitt et al. |
| D594,736 S | 6/2009 | Esjunin |
| D594,737 S | 6/2009 | Kelly et al. |
| 7,559,916 B2 | 7/2009 | Smith et al. |
| 7,608,056 B2 | 10/2009 | Kennedy, II |
| 7,611,508 B2 | 11/2009 | Yang et al. |
| D606,203 S | 12/2009 | Husheer et al. |
| D613,412 S | 4/2010 | DeCarlo |
| 7,697,972 B2 | 4/2010 | Verard et al. |
| 7,706,894 B2 | 4/2010 | Stewart et al. |
| 7,713,259 B2 | 5/2010 | Gosiengfiao et al. |
| 7,722,604 B2 | 5/2010 | Brown, III et al. |
| 7,734,330 B2 | 6/2010 | Carr |
| 7,769,469 B2 | 8/2010 | Carr et al. |
| 7,783,336 B2 | 8/2010 | Macfarlane et al. |
| 7,824,392 B2 | 11/2010 | Zhou |
| 7,826,904 B2 | 11/2010 | Appling et al. |

(56) References Cited

U.S. PATENT DOCUMENTS

| | | |
|---|---|---|
| 7,833,218 B2 | 11/2010 | Lunn et al. |
| 7,850,685 B2 | 12/2010 | Kunis et al. |
| 7,871,406 B2 | 1/2011 | Nields et al. |
| D634,010 S | 3/2011 | DeCarlo |
| 7,921,855 B2 | 4/2011 | Danek et al. |
| 7,933,660 B2 | 4/2011 | Carr |
| 7,993,351 B2 | 8/2011 | Worley et al. |
| 8,021,351 B2 | 9/2011 | Boldenow et al. |
| 8,027,712 B2 | 9/2011 | Sioshansi et al. |
| 8,075,532 B2 | 12/2011 | Kassab et al. |
| 8,152,795 B2 | 4/2012 | Farr et al. |
| 8,155,416 B2 | 4/2012 | Nields et al. |
| 8,181,995 B2 | 5/2012 | DeCarlo |
| 8,182,466 B2 | 5/2012 | Stehr et al. |
| 8,206,373 B2 | 6/2012 | Zhou |
| 8,206,380 B2 | 6/2012 | Lenihan et al. |
| 8,224,424 B2 | 7/2012 | Burbank et al. |
| 8,226,566 B2 | 7/2012 | Nita |
| 8,277,438 B2 | 10/2012 | Griffin et al. |
| 8,280,486 B2 | 10/2012 | Miller et al. |
| 8,287,463 B2 | 10/2012 | Field et al. |
| 8,289,551 B2 | 10/2012 | Wu |
| 8,292,881 B2 | 10/2012 | Brannan et al. |
| 8,303,581 B2 | 11/2012 | Arts et al. |
| 8,306,602 B2 | 11/2012 | Sirimanne et al. |
| 8,328,799 B2 | 12/2012 | Brannan |
| 8,328,800 B2 | 12/2012 | Brannan |
| 8,328,801 B2 | 12/2012 | Brannan |
| 8,340,740 B2 | 12/2012 | Holzer et al. |
| 8,343,145 B2 | 1/2013 | Brannan |
| 8,394,092 B2 | 3/2013 | Brannan |
| 8,412,306 B2 | 4/2013 | Kurpad et al. |
| D681,810 S | 5/2013 | DeCarlo |
| 8,480,665 B2 | 7/2013 | DeCarlo |
| 8,491,579 B2 | 7/2013 | Rossetto |
| 8,494,246 B2 | 7/2013 | Trumer et al. |
| 8,515,554 B2 | 8/2013 | Carr |
| 8,545,496 B2 | 10/2013 | Arts et al. |
| 8,597,291 B2 | 12/2013 | Arts et al. |
| 8,655,454 B2 | 2/2014 | Prakash et al. |
| 8,672,932 B2 | 3/2014 | van der Weide et al. |
| 8,795,268 B2 | 8/2014 | Willyard |
| 8,852,180 B2 | 10/2014 | Brannan |
| 8,906,008 B2 | 12/2014 | Brannan et al. |
| 8,920,410 B2 | 12/2014 | Brannan |
| 8,945,113 B2 | 2/2015 | Brannan et al. |
| 8,968,300 B2 | 3/2015 | Brannan |
| 9,017,328 B2 | 4/2015 | Bahney |
| 9,044,254 B2 | 6/2015 | Ladtkow et al. |
| 9,066,681 B2 | 6/2015 | Arts et al. |
| 9,119,650 B2 | 9/2015 | Brannan et al. |
| 9,161,814 B2 | 10/2015 | Brannan et al. |
| 9,168,178 B2 | 10/2015 | Reid, Jr. et al. |
| 9,192,308 B2 | 11/2015 | Brannan et al. |
| 9,192,426 B2 | 11/2015 | Brannan et al. |
| 9,192,439 B2 | 11/2015 | Dunning et al. |
| 9,192,440 B2 | 11/2015 | Rossetto |
| 9,332,959 B2 | 5/2016 | Arts et al. |
| 9,358,067 B2 | 6/2016 | Lee et al. |
| 9,364,278 B2 | 6/2016 | DeCarlo et al. |
| 9,370,392 B2 | 6/2016 | Sharonov |
| 9,375,196 B2 | 6/2016 | Zheng et al. |
| 9,439,712 B2 | 9/2016 | Sharonov |
| 9,504,524 B2 | 11/2016 | Behnke, II |
| 9,522,033 B2 | 12/2016 | Brannan |
| 9,526,568 B2 | 12/2016 | Ohri et al. |
| 9,649,146 B2 | 5/2017 | Orszulak |
| 9,662,165 B2 | 5/2017 | Sharonov |
| 9,668,802 B2 | 6/2017 | Brannan |
| 9,814,844 B2 | 11/2017 | Ohri et al. |
| 9,833,286 B2 | 12/2017 | Podhajsky |
| 9,901,398 B2 | 2/2018 | Brannan et al. |
| 10,624,697 B2 | 4/2020 | Dickhans |
| 2001/0056289 A1 | 12/2001 | Sippensgroenewegen |
| 2002/0022836 A1 | 2/2002 | Goble et al. |
| 2002/0026187 A1 | 2/2002 | Swanson |
| 2002/0049370 A1 | 4/2002 | Laufer et al. |
| 2003/0028095 A1 | 2/2003 | Tulley et al. |
| 2003/0088242 A1 | 5/2003 | Prakash et al. |
| 2003/0191451 A1 | 10/2003 | Gilmartin |
| 2004/0030262 A1 | 2/2004 | Fisher et al. |
| 2004/0049254 A1 | 3/2004 | Longo |
| 2004/0073238 A1 | 4/2004 | Makower |
| 2004/0082860 A1 | 4/2004 | Haissaguerre |
| 2004/0097805 A1 | 5/2004 | Verard et al. |
| 2004/0133254 A1 | 7/2004 | Sterzer et al. |
| 2004/0176740 A1 | 9/2004 | Chouinard |
| 2005/0015081 A1 | 1/2005 | Turovskiy |
| 2005/0043713 A1 | 2/2005 | Zhou |
| 2005/0080333 A1 | 4/2005 | Piron et al. |
| 2005/0080334 A1 | 4/2005 | Willis |
| 2005/0096502 A1 | 5/2005 | Khalili |
| 2005/0113640 A1 | 5/2005 | Saadat et al. |
| 2005/0215942 A1 | 9/2005 | Abrahamson et al. |
| 2005/0245920 A1 | 11/2005 | Vitullo et al. |
| 2005/0273006 A1 | 12/2005 | Stewart et al. |
| 2006/0004351 A1 | 1/2006 | Arless et al. |
| 2006/0009833 A1 | 1/2006 | Chobotov et al. |
| 2006/0089637 A1 | 4/2006 | Werneth et al. |
| 2006/0100614 A1 | 5/2006 | Long |
| 2006/0155270 A1 | 7/2006 | Hancock |
| 2006/0167416 A1 | 7/2006 | Mathis et al. |
| 2006/0173280 A1 | 8/2006 | Goosen et al. |
| 2006/0184016 A1 | 8/2006 | Glossop |
| 2006/0241564 A1 | 10/2006 | Corcoran et al. |
| 2006/0253102 A1 | 11/2006 | Nance et al. |
| 2006/0253126 A1 | 11/2006 | Bjerken et al. |
| 2006/0258955 A1 | 11/2006 | Hoffman et al. |
| 2007/0027385 A1 | 2/2007 | Brister et al. |
| 2007/0032723 A1 | 2/2007 | Glossop |
| 2007/0060944 A1 | 3/2007 | Boldenow et al. |
| 2007/0077230 A1 | 4/2007 | Mon |
| 2007/0088319 A1 | 4/2007 | Martone |
| 2007/0129717 A1 | 6/2007 | Brown et al. |
| 2007/0185554 A1 | 8/2007 | Appling et al. |
| 2007/0208301 A1 | 9/2007 | Evard et al. |
| 2007/0282319 A1 | 12/2007 | van der Weide et al. |
| 2007/0287912 A1 | 12/2007 | Khuri-Yakub et al. |
| 2007/0299353 A1 | 12/2007 | Harlev et al. |
| 2008/0033286 A1 | 2/2008 | Whitmore et al. |
| 2008/0033424 A1 | 2/2008 | van der Weide et al. |
| 2008/0091169 A1 | 4/2008 | Heideman et al. |
| 2008/0147056 A1 | 6/2008 | van der Weide et al. |
| 2008/0208031 A1 | 8/2008 | Kurpad et al. |
| 2008/0208039 A1 | 8/2008 | Kurpad et al. |
| 2008/0228167 A1 | 9/2008 | Mittermeyer et al. |
| 2008/0255507 A1 | 10/2008 | Mushtaha |
| 2008/0262342 A1 | 10/2008 | Averbruch |
| 2008/0262472 A1 | 10/2008 | Lunn et al. |
| 2008/0269601 A1 | 10/2008 | Schwamb |
| 2009/0005766 A1 | 1/2009 | Brannan |
| 2009/0018403 A1 | 1/2009 | Black et al. |
| 2009/0076409 A1 | 3/2009 | Wu et al. |
| 2009/0076498 A1 | 3/2009 | Saadat et al. |
| 2009/0080604 A1 | 3/2009 | Shores et al. |
| 2009/0131926 A1 | 5/2009 | Rusin et al. |
| 2009/0187180 A1 | 7/2009 | Brannan |
| 2009/0216115 A1 | 8/2009 | Seiler et al. |
| 2009/0222002 A1 | 9/2009 | Bonn et al. |
| 2009/0234220 A1 | 9/2009 | Maschke |
| 2009/0259105 A1 | 10/2009 | Miyano et al. |
| 2009/0312754 A1 | 12/2009 | Lenihan et al. |
| 2010/0004631 A1 | 1/2010 | Zhou |
| 2010/0036369 A1 | 2/2010 | Hancock |
| 2010/0053015 A1 | 3/2010 | Willyard |
| 2010/0076424 A1 | 3/2010 | Carr |
| 2010/0121319 A1 | 5/2010 | Chu et al. |
| 2010/0160719 A1 | 6/2010 | Kassab et al. |
| 2010/0185191 A1 | 7/2010 | Carr et al. |
| 2010/0234726 A1 | 9/2010 | Sirimanne et al. |
| 2010/0249754 A1 | 9/2010 | Griffin et al. |
| 2010/0262134 A1 | 10/2010 | Jensen et al. |
| 2010/0268196 A1 | 10/2010 | Hastings et al. |
| 2010/0305559 A1 | 12/2010 | Brannan et al. |

(56) References Cited

U.S. PATENT DOCUMENTS

| | | |
|---|---|---|
| 2010/0312096 A1 | 12/2010 | Guttman et al. |
| 2011/0004205 A1 | 1/2011 | Chu et al. |
| 2011/0034913 A1 | 2/2011 | Brannan |
| 2011/0034917 A1 | 2/2011 | Brannan |
| 2011/0040300 A1 | 2/2011 | Brannan |
| 2011/0046622 A1 | 2/2011 | McAuley |
| 2011/0054458 A1 | 3/2011 | Behnke |
| 2011/0066144 A1 | 3/2011 | Bonn et al. |
| 2011/0077633 A1 | 3/2011 | Bonn et al. |
| 2011/0077634 A1 | 3/2011 | Brannan |
| 2011/0077638 A1 | 3/2011 | Brannan |
| 2011/0085720 A1 | 4/2011 | Averbuch |
| 2011/0118721 A1 | 5/2011 | Brannan |
| 2011/0118723 A1 | 5/2011 | Turner et al. |
| 2011/0130750 A1 | 6/2011 | Ormsby et al. |
| 2011/0166518 A1 | 7/2011 | Nguyen et al. |
| 2011/0166519 A1 | 7/2011 | Nguyen et al. |
| 2011/0196362 A1 | 8/2011 | Rossetto |
| 2011/0200171 A1 | 8/2011 | Beetel et al. |
| 2011/0208177 A1 | 8/2011 | Brannan |
| 2011/0238083 A1 | 9/2011 | Moll et al. |
| 2011/0282336 A1 | 11/2011 | Brannan et al. |
| 2011/0301587 A1 | 12/2011 | Deem et al. |
| 2012/0029359 A1 | 2/2012 | Sterzer et al. |
| 2012/0035603 A1 | 2/2012 | Lenihan |
| 2012/0065481 A1 | 3/2012 | Hunter et al. |
| 2012/0071822 A1 | 3/2012 | Romo et al. |
| 2012/0078175 A1 | 3/2012 | Vreeman |
| 2012/0078230 A1 | 3/2012 | Lowe et al. |
| 2012/0172860 A1 | 7/2012 | Brannan |
| 2012/0259326 A1 | 10/2012 | Brannan et al. |
| 2012/0277730 A1 | 11/2012 | Salahieh et al. |
| 2013/0090552 A1 | 4/2013 | Ramamurthy et al. |
| 2013/0116679 A1 | 5/2013 | Van der Weide et al. |
| 2013/0137977 A1 | 5/2013 | Eder |
| 2013/0178841 A1 | 7/2013 | Reid, Jr. |
| 2013/0197481 A1 | 8/2013 | Guo et al. |
| 2013/0197482 A1 | 8/2013 | Akitomo |
| 2013/0225942 A1 | 8/2013 | Holsing et al. |
| 2013/0225943 A1 | 8/2013 | Holsing et al. |
| 2013/0225973 A1 | 8/2013 | Gertner |
| 2013/0225994 A1 | 8/2013 | Hsu et al. |
| 2013/0226172 A1 | 8/2013 | Peterson et al. |
| 2013/0231556 A1 | 9/2013 | Holsing et al. |
| 2013/0237980 A1 | 9/2013 | Brannan |
| 2013/0241769 A1 | 9/2013 | Brannan et al. |
| 2013/0245624 A1 | 9/2013 | Bahney |
| 2013/0253500 A1 | 9/2013 | Lee et al. |
| 2013/0261617 A1 | 10/2013 | Podhajsky |
| 2013/0261620 A1 | 10/2013 | Brannan et al. |
| 2013/0267946 A1 | 10/2013 | Brannan et al. |
| 2013/0289560 A1 | 10/2013 | DeCarlo et al. |
| 2013/0296841 A1 | 11/2013 | Brannan |
| 2013/0304057 A1 | 11/2013 | Rossetto |
| 2013/0310823 A1 | 11/2013 | Gelfand et al. |
| 2013/0317407 A1 | 11/2013 | Reid, Jr. et al. |
| 2013/0317495 A1 | 11/2013 | Brannan |
| 2013/0317499 A1 | 11/2013 | Brannan et al. |
| 2013/0324910 A1 | 12/2013 | Ohri et al. |
| 2013/0324911 A1 | 12/2013 | Ohri et al. |
| 2013/0338477 A1 | 12/2013 | Glossop et al. |
| 2013/0338661 A1 | 12/2013 | Behnke, II |
| 2013/0345541 A1 | 12/2013 | Nau, Jr. |
| 2013/0345551 A1 | 12/2013 | Arts et al. |
| 2013/0345552 A1 | 12/2013 | Arts et al. |
| 2013/0345553 A1 | 12/2013 | Arts et al. |
| 2013/0345699 A1 | 12/2013 | Brannan et al. |
| 2014/0000098 A1 | 1/2014 | Dunning et al. |
| 2014/0005655 A1 | 1/2014 | Brannan |
| 2014/0005657 A1 | 1/2014 | Brannan et al. |
| 2014/0018668 A1 | 1/2014 | Zheng et al. |
| 2014/0018677 A1 | 1/2014 | Sharonov |
| 2014/0018793 A1 | 1/2014 | Sharonov |
| 2014/0024909 A1 | 1/2014 | Vij et al. |
| 2014/0046174 A1 | 2/2014 | Ladtkow et al. |
| 2014/0046175 A1 | 2/2014 | Ladtkow et al. |
| 2014/0066922 A1 | 3/2014 | Coe et al. |
| 2014/0094789 A1 | 4/2014 | Brannan |
| 2014/0094792 A1 | 4/2014 | Sharonov |
| 2014/0094794 A1 | 4/2014 | Orszulak |
| 2014/0094797 A1 | 4/2014 | Brannan |
| 2014/0296875 A1 | 10/2014 | Moll et al. |
| 2015/0022342 A1 | 1/2015 | Will et al. |
| 2015/0038956 A1 | 2/2015 | Amabile |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 3/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1034747 A1 | 9/2000 |
| EP | 1034748 A1 | 9/2000 |
| EP | 1055400 A1 | 11/2000 |
| EP | 1159926 A2 | 3/2003 |
| EP | 2060239 A1 | 5/2009 |
| EP | 2098184 A1 | 9/2009 |
| EP | 2147651 A1 | 1/2010 |
| EP | 2322113 A1 | 5/2011 |
| FR | 179 607 | 11/1906 |
| FR | 1275415 A | 11/1961 |
| FR | 1347865 A | 1/1964 |
| FR | 2 235 669 A1 | 1/1975 |
| FR | 2 276 027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |

(56) References Cited

FOREIGN PATENT DOCUMENTS

| | | | |
|---|---|---|---|
| FR | 2 862 813 A1 | 5/2005 | |
| FR | 2 864 439 A1 | 7/2005 | |
| JP | 55106 | 1/1993 | |
| JP | H0540112 A | 2/1993 | |
| JP | H06343644 A | 12/1994 | |
| JP | H07265328 A | 10/1995 | |
| JP | 08252263 A | 10/1996 | |
| JP | 09000492 A | 1/1997 | |
| JP | H0910223 A | 1/1997 | |
| JP | H11244298 A | 9/1999 | |
| JP | 2000342599 A | 12/2000 | |
| JP | 2000350732 A | 12/2000 | |
| JP | 2001003776 A | 1/2001 | |
| JP | 2001008944 | 1/2001 | |
| JP | 2001029356 | 2/2001 | |
| JP | 2001037775 A | 2/2001 | |
| JP | 2001128990 A | 5/2001 | |
| JP | 2001231870 A | 8/2001 | |
| JP | 2001518351 A | 10/2001 | |
| JP | 2005507736 A | 3/2005 | |
| JP | 2008142467 A | 6/2008 | |
| JP | 2009207898 A | 9/2009 | |
| JP | 2010110579 A | 5/2010 | |
| JP | 2011516184 A | 5/2011 | |
| JP | 2012139496 A | 7/2012 | |
| JP | 2012187405 A | 10/2012 | |
| KR | 20070093068 A | 9/2007 | |
| KR | 20100014406 A | 2/2010 | |
| KR | 20120055063 A | 5/2012 | |
| SU | 166452 | 11/1964 | |
| SU | 401367 A1 | 10/1973 | |
| SU | 727201 A2 | 4/1980 | |
| WO | 9416632 A1 | 8/1994 | |
| WO | 9724074 A1 | 7/1997 | |
| WO | 0010456 A1 | 3/2000 | |
| WO | 0036985 A2 | 6/2000 | |
| WO | 0057811 A1 | 10/2000 | |
| WO | 0100114 A1 | 1/2001 | |
| WO | 0167035 A1 | 9/2001 | |
| WO | 02/45790 A2 | 6/2002 | |
| WO | 2002061880 A2 | 8/2002 | |
| WO | 2006084676 A1 | 8/2006 | |
| WO | WO-2006084676 A1 * | 8/2006 | ............ A61B 18/18 |
| WO | 2008068485 A2 | 6/2008 | |
| WO | 2010035831 A1 | 4/2010 | |
| WO | 2011063061 A2 | 5/2011 | |
| WO | 2012071388 A2 | 5/2012 | |
| WO | 2014/025549 A1 | 2/2014 | |
| WO | 2014025551 A1 | 2/2014 | |

OTHER PUBLICATIONS

Canadian Office Action issued in correspdong application CA 2,959,337 dated Jul. 8, 2021 (6 pages).
Extended European Search Report issued in corresponding application EP 22179318.5 dated Jul. 13, 2022 (10 pages).
Sengupta et al., "Use of a Computer-Controlled Bipolar Diathermy System in Radical Prostatectomies and Other Open Urological Surgery" ANZ Journal of Surgery (2001)71.9 pp. 538-540.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Valleylab Brochure, "Valleylab Electroshield Monitoring System" 2 pages, Nov. 1995.
Vallfors et al., "Automatically Controlled Bipolar Electrocoagulation-'COA-COMP" Neurosurgical Review 7:2-3 (1984) pp. 187-190.
Wald et al., "Accidental Burns", JAMA, Aug. 16, 1971, vol. 217, No. 7, pp. 916-921.
U.S. Appl. No. 08/136,098, filed Oct. 14, 1993, Roger A. Stem.
U.S. Appl. No. 08/483,742, filed Jun. 7, 1995, Roger A. Stem.
Extended European Search Report issued in Appl. No. EP 15836982.7 dated Mar. 20, 2018.
Chinese Office Action issued in Appl. No. CN 201580049301.6 dated Nov. 5, 2018, together with English language translation (20 pages).
Japanese Office Action issued in corresponding Appl. No. JP 2017-510883, together with English language translation, dated Aug. 23, 2019 (5 pages).
European Search Report, Application No. EP 14 16 0223 dated Jun. 3, 2014.
European Search Report, Application No. EP 14 16 0251 dated Sep. 25, 2014.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1999) MIBB Site Marker, United States Surgical (Sales brochure), 4 pages.
B. F. Mullan et al., (May 1999) "Lung Nodules: Improved Wire for CT-Guided Localization," Radiology 211:561-565.
Bulletin of the American Physical Society, vol. 47, No. 5, Aug. 2002, p. 41.
Cosman et al., "Radiofrequency Lesion Generation and its Effect on Tissue Impedence", Applied Neurophysiology, 51:230-242, 1988.
Crawford et al., "Use of the LigaSure.TM. Vessel Sealing System in Urologic Cancer Surger" Grand Rounds in Urology 1999, vol. 1, Issue 4, pp. 10-17.
Esterline, "Light Key Projection Keyboard" Advanced Input Systems, located at: <http://www.advanced-input.com/lightkey> 2002.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Heniford et al., "Initial Results with an Electrothermal Bipolar Vessel Sealer" Surgical Endoscopy (2001) 15:799-801.
Jarrett et al., "Use of the LigaSureTM Vessel Sealing System for Peri-Hilar Vessels in Laparoscopic Nephrectomy" Sales/Product Literature 2000.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Joseph Ortenberg, "LigaSureTM System Used in Laparoscopic 1st and 2nd Stage Orchiopexy" Innovations That Work, Nov. 2002.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
Livraghi et al., (1995) "Saline-enhanced RF Tissue Ablation in the Treatment of Liver Metastases", Radiology, p. 140 (Abstr).
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.

(56) References Cited

OTHER PUBLICATIONS

MDTech product literature (Dec. 1999) "FlexStrand": product description, 1 page.
MDTech product literature (Mar. 2000) I'D Wire: product description, 1 page.
Murakami, R. et al., (1995). "Treatment of Hepatocellular Carcinoma: Value of Percutaneous Microwave Coagulation," American Journal of Radiology (AJR) 164:1159-1164.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Peterson et al., "Comparison of Healing Process Following Ligation with Sutures and Bipolar Vessel Sealing" Surgical Technology International (2001).
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'L Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
T. Matsukawa et al., "Percutaneous Microwave Coagulation Therapy in Liver Tumors", Acta Radiologica, vol. 38, pp. 410-415, 1997.
Urrutia et al., (1988). "Retractable-Barb Needle for Breast Lesion Localization: Use in 60 Cases," Radiology 169(3):845-847.
ValleyLab Brochure, "Electosurgery: A Historical Overview", Innovations in Electrosurgery, 1999.
W. Scott Helton, "LigaSureTM Vessel Sealing System: Revolutionary Hemostasis Product for General Surgery" Sales/Product Literature 1999.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
Australian Examination Report issued in corresponding Appl. No. AU 2015306746 dated May 2, 2019 (3 pages).
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology. vol. 102, No. 1, Jul. 2003.
B. Levy M.D. et al., "Update on Hysterectomy New Technologies and Techniques" OBG Management. Feb. 2003.
B. Levy M.D.. "Use of a New Vessel Ligation Device During Vaginal Hysterectomy" FIGO 2000, Washington, D.C.

B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1, (Jul. 1991) pp. 148-151.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al.. "Antennas for Medical Applications", Antenna Handbook: Theory Application and Design, p. 24-40. Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, CarolinasMedicalCenter, Chartotte, NC 2003.
Carus et al., "Initial Experience With the LigaSure. TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52. No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions", In William RH, Rengachary SS (eds): Neurosurgery, New York: McGraw-Hill, vol. 111, (1984), pp. 2490-2499.
Cosman et al., "Theoretical Aspects of Radiofrequency Lesions in the Dorsal Root Entry Zone", Neurosurgery 15: (1984) pp. 945-950.
Dulemba et al. "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts". Nov. 1, 2003; 4 pages.
Geddes et al.. "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf Germany; Dec. 8, 1994; pp. 729-731.
Herman at al., "Laparoscopic Intestinal Resection With the LigaSureTM Vessel Sealing System: A Case Report" Innovations That Work, Feb. 2002.
Humphries Jr. et al., "Finite.cndot. Element Codes to Model Electrical Heating and Non.cndot.Linear Thermal Transport in Biological Media", Proc. Asme HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands. vol. 4; No. 1. pp. 307-320.
Johnson et al. "Evaluation of a Bipolar Electrothermal Vessel Sealing Device in Hemorrhoidectomy" Sales/Product Literature; Jan. 2004.
Johnson, "Use of the LigaSureTM Vessel Sealing System in Bloodless Hemorrhoidectomy" Innovations That Work, Mar. 2000.
Joseph G. Andriole, M.D., et al., "Biopsy Needle Characteristics Assessed in the Laboratory", Radiology 148: 659-662, Sep. 1983.
Kennedy et al. "High-burst-strength, feedback-controlled bipolar vessel sealing" Surgical Endoscopy (1998) 12:876-878.

(56) References Cited

OTHER PUBLICATIONS

LigaSureTM Vessel Sealing System, the Seal of Confidence in General, Gynecologic, Urologic, and Laparaoscopic Surgery, Sales/Product Literature, Jan. 2004.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May-Jun. 1982.
Euorpean Search Report, Application No. EP 14 16 0251 dated Sep. 25, 2014.
European Search Report, Application No. EP 14 16 0222 dated May 28, 2014.
Japanese Office Action, Application No. 2014-104075 dated May 19, 2015.
International Search Report corresponding to PCT/US2013/052166, completed Nov. 15, 2013 and dated Nov. 18, 2013; (12 pp).
International Search Report corresponding to PCT/US2013/052182, completed Nov. 6, 2013 and dated Nov. 6, 2013; (14 pp).
International Search Report corresponding to PCT/US2013/052187, completed Nov. 4, 2013 and dated Nov. 4, 2013; (19 pp).
International Search Report corresponding to PCT/US2013/052196, completed Nov. 11, 2013 and dated Nov. 11, 2013; (21 pp).
U.S. Appl. No. 13/942,833, filed Jul. 16, 2013, Sharonov.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Anonymous. (1987) Homer Mammalok. TM. Breast Lesion Needle/Wire Localizer, Namic.RTM. Angiographic Systems Division, Glens Falls, New York, (Hospital products price list), 4 pages.
International Search Report and Written Opinion from Appl. No. PCT/US2015/046729 dated Dec. 1, 2015.
Medtrex Brochure "The O.R. Pro 300" 1 page; Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Ni Wei et al., "A Signal Processing Method for the Coriolis Mass Flowmeter Based on a Normalized . . . " Journal of Applied Sciences.cndot. Yingyong Kexue Xuebao, Shangha CN, vol. 23, No. 2:(Mar. 2005); pp. 160-184.
Ogden, "Goertzel Alternative to the Fourier Transform": Jun. 1993 pp. 485-487 Electronics World; Reed Business Publishing, Sutton, Surrey, BG, vol. 99, No. 9, 1687.
Olsson M.D et al., "Radical Cystectomy in Females" Current Surgical Techniques in Urology, vol. 14, Issue 3, 2001.
Palazzo et al., "Randomized clinical trial of LigaSureTM versus open haemorrhoidectomy" British Journal of Surgery 2002, 89, 154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001 pp. 236-237.
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure. "Reducing Needlestick Injuries in the Operating Room" 1 page, Mar. 2001.
European Examination Report issued in corresponding application EP 22179318.5 dated Jan. 26, 2024 (5 pages).

* cited by examiner

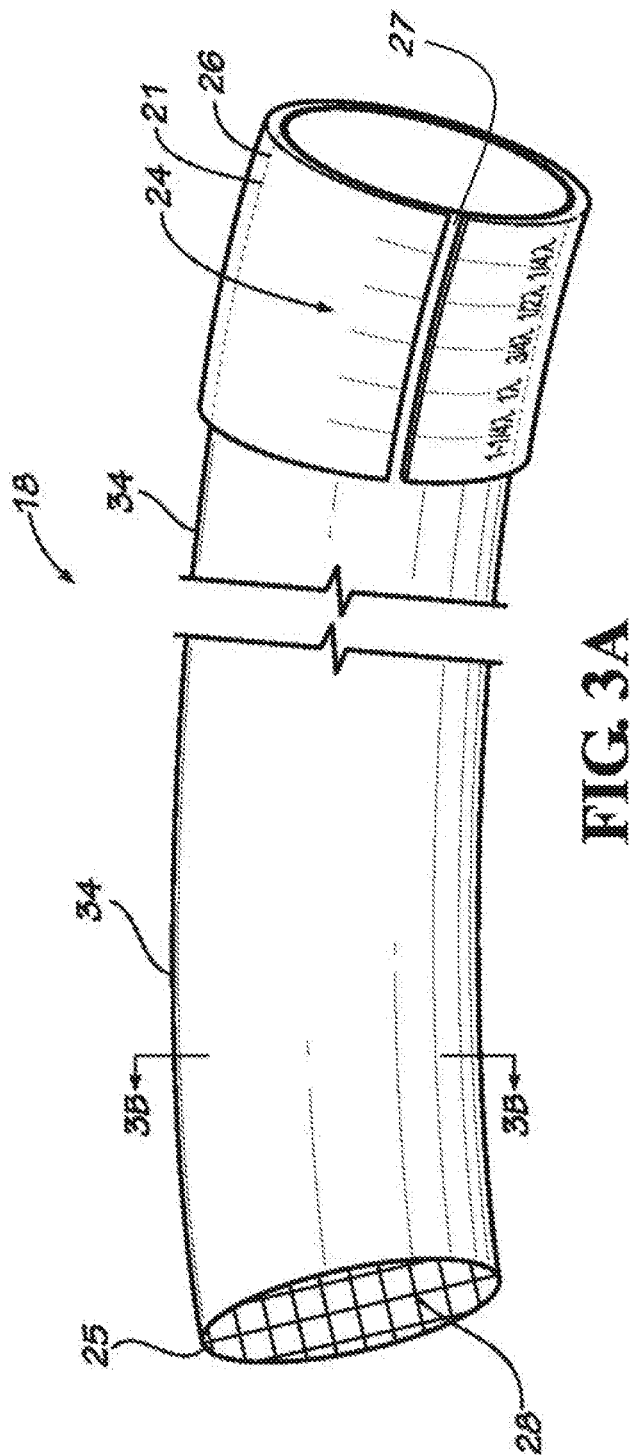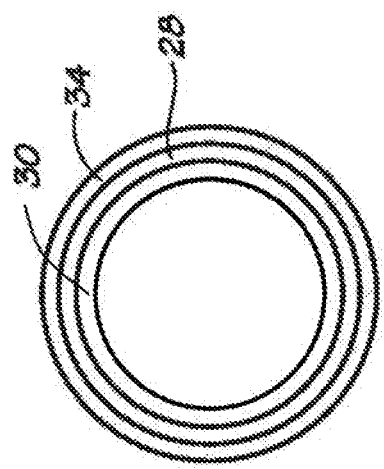
FIG. 3A
FIG. 3B

MICROWAVE ABLATION SYSTEM

CROSS REFERENCE TO RELATED APPLICATIONS

This application is a continuation of U.S. application Ser. No. 14/828,682, filed Aug. 18, 2015, now U.S. Pat. No. 10,624,697, which claims the benefit of the filing date of provisional U.S. Patent Application No. 62/041,773, filed Aug. 26, 2014.

BACKGROUND

The present disclosure relates to a microwave ablation catheter assembly. More particularly, the present disclosure relates to a microwave ablation catheter assembly including an extended working channel having an electrically conductive inner surface that functions as an electromagnetic shield or a balun for a microwave ablation catheter of the microwave ablation catheter assembly.

Microwave ablation involves the application of high-frequency electromagnetic waves for treating various maladies including tumors in of organs like the liver, brain, heart, lung and kidney. It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods may involve applying electromagnetic radiation, or microwave energy, to heat tissue and include ablation and coagulation of tissue. In particular, microwave energy is used to ablate tissue to denature or kill the cancerous cells.

Conventional microwave ablation systems typically include one or more microwave ablation catheters coupled to a microwave energy source via a feedline, typically in the form of a coaxial cable. The microwave ablation catheters are placed adjacent target tissue and microwave energy is applied to the microwave ablation catheters causing localized heating of target tissue. The microwave ablation catheter is typically relatively thin and flexible to allow a user to navigate the microwave ablation catheter through a luminal network of one of the aforementioned organs, e.g., a lung.

When treating malignancies of the lung, microwave ablation systems are often used in conjunction with an electromagnetic navigation (EMN) system. One such system is described in U.S. Pat. No. 6,188,355 and published PCT Application Nos. WO 00/10456 and WO 01/67035, the entire contents of which are hereby incorporated by reference. An EMN system typically includes a bronchoscope, a catheter assembly containing a location sensor at its steerable distal tip, an extended working channel that extends beyond the reach of the bronchoscope and becomes a pathway to the target site for subsequent diagnostic tools, and a computer system which provides the physician, or user, with navigational views of the lung. Once the bronchoscope is inserted into a patient's lungs, the catheter assembly with the extended working channel is inserted into the bronchoscope. Using the navigation system and the steerable distal tip, the catheter assembly and extended working channel is navigated to a target location. The catheter assembly is then removed, leaving the extended working channel in place. The microwave ablation catheter can then be inserted into the extended working channel and directed to the target location.

As previously mentioned, the microwave ablation catheter is coupled to the microwave energy source via a feedline, often in the form of an unbalanced coaxial cable. As a result of the coaxial cable being unbalanced, there is often a loss of microwave energy along the coaxial cable. Additionally, substantial heating of the coaxial cable can occur during delivery of microwave energy. In order to help minimize the loss of energy as a result of an unbalanced coaxial cable, microwave ablation catheters that utilize a feedline in the form of a coaxial cable may include a balun or choke. The balun or choke helps to balance the coaxial cable of the microwave ablation catheter when microwave energy is transmitted to the radiating section of the microwave ablation catheter to ablate tissue and substantially impede the current flowing down the outer conductor which might lead to undesired heating of tissue along the length of the ablation catheter.

While the aforementioned microwave ablation catheters are suitable for their intended purposes, the balun on the microwave ablation catheter is added structure that increases the size of the microwave ablation catheter, which, in turn, may decrease the flexibility of the microwave ablation catheter.

SUMMARY

As can be appreciated, an extended working channel having an electrically conductive inner surface that functions as an electromagnetic shield and/or a balun for a microwave ablation catheter of a microwave ablation system may prove useful in the surgical arena.

Aspects of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

As defined herein braided means made by intertwining three or more strands, and while described as a braid, the actual construction is not so limited and may include other formations as would be understood by those of ordinary skill in the art.

An aspect of the present disclosure provides a microwave ablation catheter assembly comprising an ablation catheter and an extended working channel. The ablation catheter includes a coaxial cable having a proximal portion and a distal portion and a radiator disposed at the distal portion of the coaxial cable. The coaxial cable further includes an inner conductor and an outer conductor. The proximal portion of the coaxial cable is capable of being operatively connected to a microwave energy source. The extended working channel is configured to receive the ablation catheter for positioning the radiator adjacent target tissue. The extended working channel includes an electrically conductive inner surface, wherein, upon application of microwave energy to the microwave ablation catheter assembly, energy conducted along the outer conductor of the coaxial cable is captured within the conductive inner surface of the extended working channel and prevented from affecting tissue adjacent the extended working channel.

The microwave ablation catheter assembly, including the ablation catheter and extended working channel, may me placed within a patient using a location sensing system. The extended working channel may also include a slot at its proximal end configured to releasably engage with a corresponding mechanical interface positioned on the ablation catheter. The mechanical interface may also be configured to be moveable with the slot to lock the distal radiating section of the coaxial cable into at least one of a plurality of positions defined within the slot. Indicia may also be provided along the slot and may be configured to represent quarter-wavelength increments. The extended working channel may further comprise an insulator separating the electrically conductive inner surface from tissue adjacent the extended working channel.

The ablation catheter of the microwave ablation catheter assembly may further include one or more cooling catheters surrounding the coaxial cable and radiator to provide a pathway for a cooling medium, such as a gas or liquid. The extended working channel may also provide for an open or closed pathway for a cooling medium to either circulate within or pass through the extended working channel.

An aspect of the instant disclosure provides a method of electrosurgically treating target tissue. An extended working channel, having at least a portion of an electrically conductive inner surface, is positioned adjacent target tissue. Thereafter, an ablation catheter, having an outer conductor, is inserted through the extended working channel such that a radiator of the ablation catheter extends beyond the distal end of the extended working channel. Energy is then applied to the ablation catheter such that the electrosurgical energy radiates from the radiator to electrosurgically treat the target tissue. Upon application of energy to the ablation catheter, any energy conducted along an outer conductor of the ablation catheter is captured within the electrically conductive inner surface of the extended working channel, preventing the energy from affecting tissue adjacent the extended working channel.

The method of electrosurgically treating target tissue may further include engaging a mechanical interface of the ablation catheter with at least one mechanical interface defined along a slot provided on the extended working channel to lock the radiator of the ablation catheter in a position that is distal of the distal end of the extended working channel. The slot may be provided at a proximal end of the extended working channel and may be configured to releasably couple to a mechanical interface positioned on the ablation catheter. Indicia may further be provided along the slot which may represent quarter-wavelength increments. The method may further include moving the mechanical interface of the ablation catheter distally to lock the ablation catheter into at least one other position within the slot to adjust a signal balance between inner and outer conductors of the ablation catheter. The electrically conductive inner surface of the extended working channel may further include a braided configuration.

An aspect of the present disclosure provides a microwave ablation system. The microwave ablation system comprises a microwave energy source, an ablation catheter, and an extended working channel. The ablation catheter includes a coaxial cable, having a proximal portion and a distal portion, and a radiator disposed at the distal portion of the coaxial cable. The coaxial cable includes an inner conductor and an outer conductor, and the proximal portion of the coaxial cable is operatively connected to the microwave energy source. The extended working channel is configured to receive the ablation catheter for positioning the radiator adjacent target tissue. The extended working channel includes an electrically conductive inner surface, wherein, upon application of microwave energy to the ablation catheter, energy conducted along the outer conductor of the coaxial cable is captured within the conductive inner surface of the extended working channel and prevented from affecting tissue adjacent the extended working channel

BRIEF DESCRIPTION OF THE DRAWINGS

Various embodiments of the present disclosure are described herein with references to the drawings, wherein:

FIG. 3A is a perspective view of the distal and proximal portions of an extended working channel of a catheter guide assembly shown in FIG. 1;

FIG. 3B is a transverse, cross-sectional view of one embodiment of the extended working channel shown in FIG. 3A.

DETAILED DESCRIPTION

The present disclosure is directed to a microwave ablation catheter assembly and a method for placement of a microwave ablation antenna within a luminal structure such as the pathways of the bronchi in the lungs. Embodiments of the present disclosure include an unchoked microwave ablation catheter, or microwave ablation catheter without a balun. Further embodiments are directed to a microwave ablation catheter with a modified balun or choke. Still further embodiments of the present disclosure are directed to an improved microwave ablation catheter assembly having increased flexibility and a reduced number of components while providing adequate therapeutic results.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
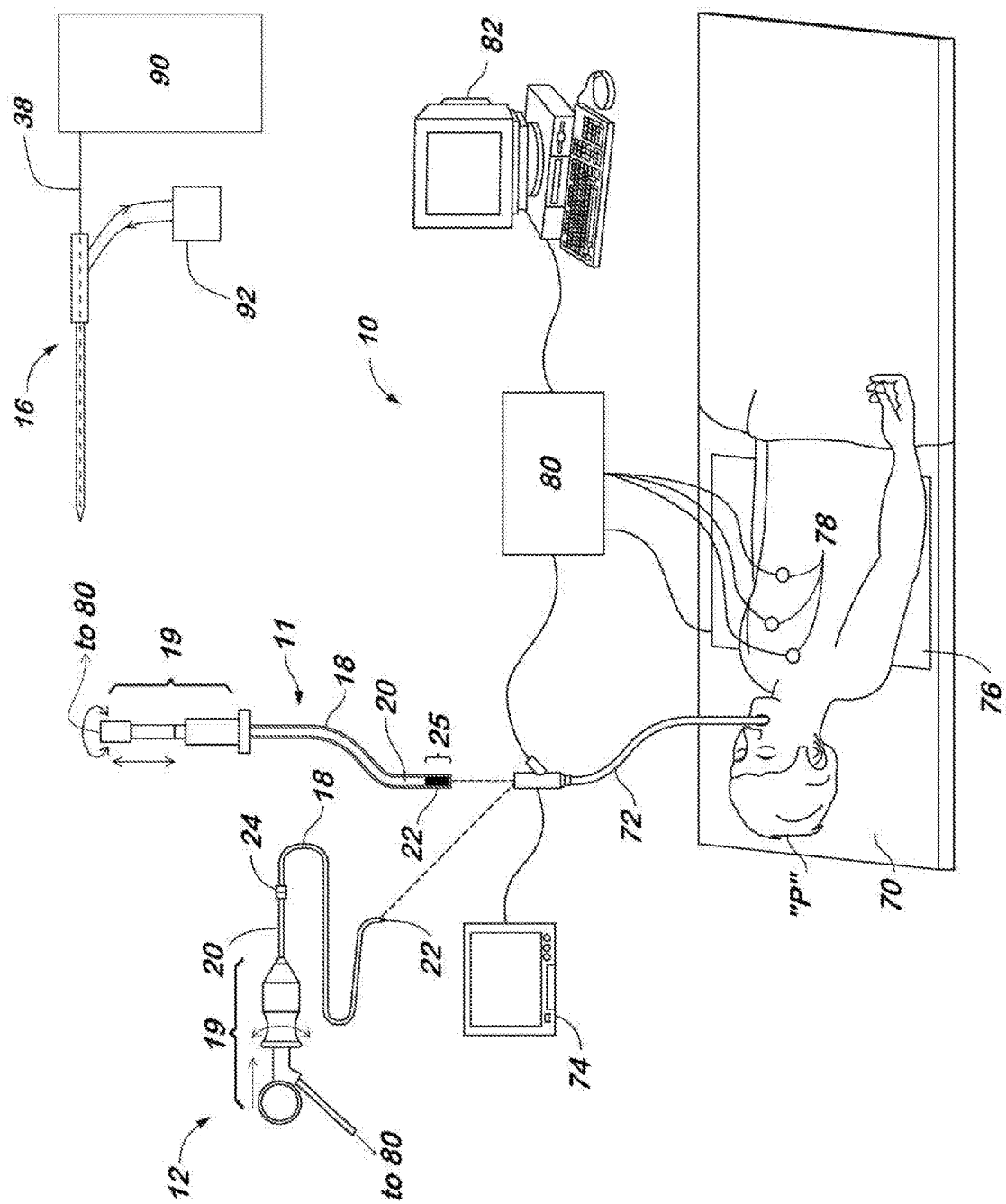
FIG. 1 is a schematic illustration of an EMN system configured for use with a microwave ablation catheter in accordance with an illustrative embodiment of the present disclosure.

FIG. 1 is an illustration of an EMN system 10 in accordance with the present disclosure. One such EMN system 10 is the ELECTROMAGNETIC NAVIGATION BRONCHOSCOPY® system currently sold by Covidien LP. Typically the EMN system 10 includes a bronchoscope 72, one or more of two different types of catheter guide assemblies 11 and 12, monitoring equipment 74, an electromagnetic field generator 76, a tracking module 80, and a computer system 82. FIG. 1 shows a patient "P" lying on an operating table 70 including an electromagnetic field generator 76. Placed on the patient "P" are a number of sensors 78, whose position in the magnetic field generated by the electromagnetic field generator 76 can be determined by the tracking module 80.

Each of the catheter guide assemblies 11, 12 includes an extended working channel 18 that is configured to receive a locatable guide catheter 20 which includes a sensor 22. The locatable guide catheter 20 is electrically connected to the EMN system 10, and particularly, the tracking module 80 enables navigation and tracking of the sensor 22 within a luminal network, such as the lungs of a the patient "P", to arrive at a designated target. As will be described in greater detail below, the extended working channel 18 is configured to receive instruments including the locatable guide catheter 20 and sensor 22, biopsy tools and microwave ablation catheter 16, as well as others without departing from the scope of the present disclosure.

Figure 2:
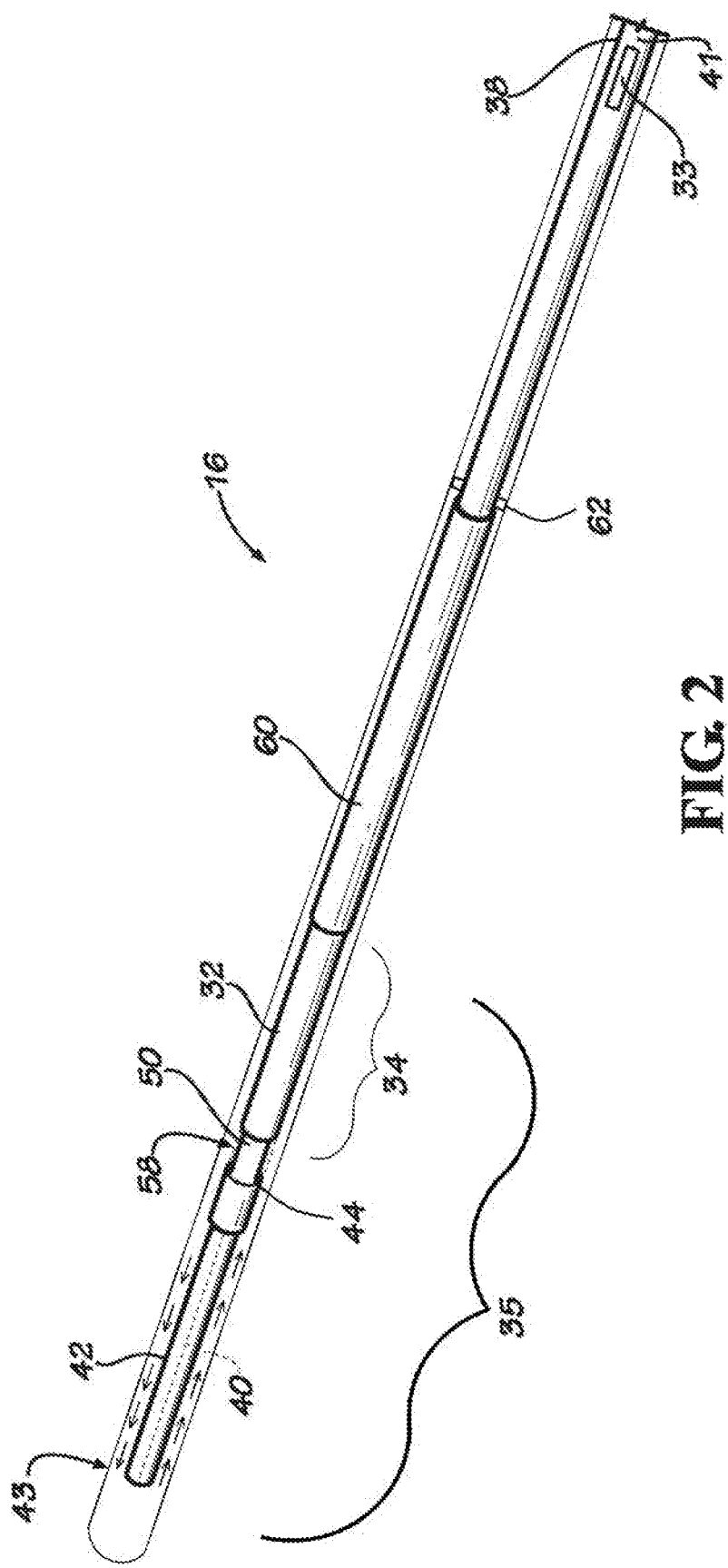
FIG. 2 is a perspective view of a microwave ablation catheter in accordance with an embodiment of the instant disclosure.

FIGS. 1 and 2 depict an ablation catheter 16 in accordance with one embodiment of the present disclosure. The ablation catheter 16 includes a coaxial cable 38. Coaxial cable 38 includes a proximal end 41 that couples to a microwave energy source 90 (FIG. 1). A cooling source 92 connects to the ablation catheter 16 to circulate cooling fluid as will be described in greater detail below. As shown in greater detail in FIG. 2, a distal radiating section 42 is provided at a distal end 44 of the coaxial cable 38 and is configured to receive the inner conductor 40. The distal radiating section 42 may be formed from any suitable material. For example, in embodiments, the distal radiating section 42 may be formed from ceramic or metal, e.g., copper, gold, silver, etc. The distal radiating section 42 may include any suitable configuration including but not limited to a blunt configuration, flat configuration, hemispherical configuration, pointed configuration, bar-bell configuration, tissue piercing configuration, etc. The distal radiating section 42 may couple to the distal end 44 of the coaxial cable via soldering, ultrasonic welding, adhesive, or the like. In one embodiment the distal radiating section 42 is sealed to the inner conductor 40 to prevent fluid from contacting the inner conductor 40.

Proximate the distal radiating section 42 is a feed gap 58, which is formed by removing a portion of the outer conductor 32 of the coaxial cable 38, to expose a dielectric 50. Proximate the feed gap 58 is the proximal radiating section 34, which is essentially just a portion of the outer conductor 32 of the coaxial cable 38. The proximal radiating section 34, the feedgap 58, and the distal radiating section 42 are located and dimensioned to achieve a specific radiation pattern for the ablation catheter 16 and in combination are collectively known as the radiator 35 of the ablation catheter 16. As will be explained in greater detail below, the extension of the radiator 35 out of the extended working channel 18 enables the ablation of tissue, but the length of that extension can be varied as desired to adjust the shape and size of the ablation zone.

The outer conductor 32 is typically formed of a braided electrically conducting material and extends along the dielectric 50, which is positioned between the inner and outer conductors 40 and 32, respectively. One advantage of a braided configuration of the outer conductor 32 is that it provides the ablation catheter 16 with the flexibility to move within the relatively narrow luminal structures such as the airways of the lungs of a patient. Additionally, through the use of flat wire braiding and follow on braid compression with an appropriately sized die, the cross sectional dimension of the braided conductor may be minimized significantly in comparison to other conductive structures, while maintaining an acceptable electrical performance. The ablation catheter 16 may include one or more cooling catheters 43 surrounding the coaxial cable 38 and radiator 35, these cooling catheters 43 enable the passage of cooling medium over the coaxial cable 38 and the radiator 35. The cooling catheters provide pathways for cooling liquid or gas to reach the distal radiating section and remove heat generated by the application of energy. Cooling the radiator 35 and the coaxial cable 38 helps ensure that the ablation process is undertaken by the radiating waves of electromagnetic energy heating the tissue and not by localized heating of the coaxial cable 38 or distal radiating section 42. Though shown in FIG. 2 with a single cooling catheter 43, those of skill in the art will appreciate that additional co-luminal catheters may be employed to enable bi-directional cooling medium flow with cooling medium passing the coaxial cable 38 and a first cooling catheter in a distal direction, reaching an area proximate the distal end of the ablation catheter and then returning in a proximate direction between the first and a second cooling catheter. Further, as will be appreciated by those of skill in the art, the cooling catheters 43 are not entirely necessary and ablation catheter 16 may be utilized in an uncooled or open cooled system as will be described in greater detail below.

The flexibility of the ablation catheter 16 can be altered to accommodate a specific surgical procedure, a specific luminal structure, specific target tissue, a clinician's preference, etc. For example, in an embodiment, it may prove advantageous to have an ablation catheter 16 that is very flexible for movement through the relatively narrow airway of the lungs of a patient. Alternatively, it may prove advantageous to have an ablation catheter 16 include portions which are less flexible, e.g., where the ablation catheter 16 is needed to pierce or puncture target tissue.

One of the effects of ablation catheters is an energy loss that occurs as energy intended for radiation into the tissue via the radiator 35 is reflected and/or travels proximally along the outer conductor 32 of the coaxial cable 38, resulting in a less efficient system. In some instances this energy can cause heating along the length of the catheter, and affect the tissue proximate the outer conductor 32. As noted above, one methodology for preventing the traversal of this energy along the outer conductor is to employ a balun or choke which effectively causes the energy to be reflected back towards the distal radiating section 42, and provide useful energy for the ablation process, rather than be an energy loss in the system. Methods of forming a balun for a flexible ablation catheter are described in U.S. patent application Ser. No. 13/834,581, filed on Mar. 15, 2013 by Brannan et al. entitled "Microwave Energy-Delivery Device and System," the entire contents of which are hereby incorporated by reference.

However, to improve the flexibility of the ablation catheter 16, one embodiment of the present disclosure does not employ a balun or choke. Instead, the ablation catheter 16, as shown in FIG. 2, relies on the construction of the components of the catheter guide assemblies 11 and 12, and particularly the extended working channel 18 to control the emission of microwave energy from the ablation catheter 16, substantially contain the energy traveling down the outer conductor 32, and prevent that energy from affecting tissue.

To further clarify how the construction of the catheter guide assemblies 11, 12 affect the emission of microwave energy, reference is made to FIG. 1 which depicts two types of catheter guide assemblies 11, 12. Both catheter guide assemblies 11, 12 are usable with the EMN system 10 and share a number of common components. Each catheter guide assembly 11, 12 includes a handle 19, which is connected to an extended working channel 18. The extended working channel 18 is sized for placement into the working channel of a bronchoscope 72. In operation, a locatable guide 20, including an electromagnetic sensor 22, is inserted into the extended working channel 18 and locked into position such that the sensor 22 extends a desired distance beyond the distal tip 25 of the extended working channel 18.

The location of the sensor 22, and thus the distal end of the extended working channel 18, within an electromagnetic field generated by the electromagnetic field generator 76 can be derived by the tracking module 80, and the computer system 82. Catheter guide assemblies 11, 12 have different operating mechanisms, but each contain a handle 19 that can be manipulated by rotation and compression to steer the distal tip 25 of the extended working channel 18 and/or the sensor 22 at the distal end of the locatable guide 20. Catheter guide assemblies 11 are currently marketed and sold by Covidien LP under the name SUPERDIMENSION® Procedure Kits. Similarly, catheter guide assemblies 12 are currently sold by Covidien LP under the name EDGE™ Procedure Kits. Both kits include a handle 19, extended working channel 18, and locatable guide 20. For a more detailed description of the catheter guide assemblies including handle 19, extended working channel 18, locatable guide 20, and sensor 22, reference is made to commonly-owned U.S. patent application Ser. No. 13/836,203 filed on Mar. 15, 2013 by Ladtkow et al, the entire contents of which are hereby incorporated by reference.

As shown in FIG. 3A, the extended working channel 18 includes a conductive inner layer 28 and an insulating layer 34. When an ablation catheter 16 is inserted into the extended working channel 18, such that the radiator 35 extends beyond the distal end 25 of the extended working channel 18, and microwave energy is applied through the coaxial cable 38 to the radiator, the conductive inner layer 28 forms an electromagnetic barrier preventing the radiation of the energy traveling down the outer conductor 32 from radiating to the tissue contacting the insulating layer 34. Essentially the conductive inner layer 28 creates a Faraday cage, significantly limiting the transmission of the energy through the extended working channel 18. The insulating layer 34 provides for additional separation of the energy from the tissue. Finally, any localized heating is effectively removed by the passage of the cooling medium along the outer conductor 32 through cooling catheter 43. The result of such an arrangement with the cooled ablation catheter 16 housed within the extended working channel 18 is that greater flexibility in the ablation catheter 16 can be achieved due to the absence of a balun, without experiencing the localized heating drawbacks which can affect ablation catheters without the emissions controlling features of a balun.

Referring to FIGS. 3A and 3B, partial views of the extended working channel 18 are shown. In one embodiment, the extended working channel is formed of two layers, a non-conductive or insulative outer layer 34 and a conductive inner layer 28. Insulating layer 34 may be formed of a medical grade flexible plastic or polymer material. The conductive inner layer 28 may be formed of a braided metallic material and substantially secured to the inner surface of the insulating layer and extends along the entire length of the inner wall of the extended working channel 18. Though depicted in FIG. 3B as concentric layers, the conductive inner layer 28 could also be imbedded in the insulative outer layer 34. The extended working channel 18 may be formed by overmolding plastic to form an outer non-conductive or insulative layer 34. The extended working channel 18 has a proximal end 21 and a distal tip 25, respectively. The extended working channel 18 is formed to receive the ablation catheter 16 (shown in FIG. 2), and, in at least one embodiment, to provide a pathway for a cooling medium to either circulate within the extended working channel 18, or to pass through the extended working channel, in both instances to cool the ablation catheter 16 when energized.

In one embodiment, a hub portion 26 is formed at the proximal end 21 of the extended working channel 18 and includes a locking mechanism 24 configured to engage the ablation catheter 16. The locking mechanism 24 may include a slot 27 that extends along the hub portion 26. The slot 27 includes a plurality of mechanical interfaces 29 (shown in FIG. 4) positioned along the opposing wall portions that define the slot 27. The mechanical interfaces 29 may be in the form of detents, protrusions, or the like that are configured to releasably engage a corresponding mechanical interface 33 (shown in FIGS. 2 and 4) provided at a proximal end of the ablation catheter 16. Engagement between the mechanical interface 33 and the plurality of mechanical interfaces 29 selectively locks the ablation catheter 16 into place within the extended working channel 18. As will be appreciated, other locking mechanisms may be employed within the scope of the disclosure.

In the embodiment of FIG. 3A, indicia are provided along the slot 27 adjacent the mechanical interfaces 29 (shown in FIG. 4) of the slot 27 and represent quarter-wavelength increments of a desired frequency of a signal transmitted from the ablation catheter 16. In embodiments, each mechanical interface 29, starting with the first mechanical interface 29, represents a quarter-wavelength value; thus, the first mechanical interface 29 represents a quarter-wavelength, the second mechanical interface represents a half-wavelength, and so on. The selection of quarter wave increments may enable the ablation catheter 16 and its use to be tuned to achieve a particularly desired ablation pattern.

Though described above with reference to an unchoked ablation catheter, the ablation catheter 16 may also incorporate a modified choke, as described in various embodiments below, without departing from the scope of the present disclosure. For example, in some embodiments, as shown in FIG. 2 a thin layer of insulating material 60 (e.g., a layer of polyethylene terephthalate (PET)) may be used to cover a portion of the outer conductor 32. This layer of insulating material 60 may assist in maintaining the braided configuration of the outer conductor 32, or may form part of a modified balun configuration.

In such a modified choke, the conductive inner layer 28 is only provided in a portion of the extended working channel 18. The electrically conductive inner layer 28 is shorted to the outer conductor 32 of the microwave ablation catheter 16 at a desired location immediately proximal a proximal end of the insulating material 60, thus creating a choke or balun by the combination of the conductive inner layer 28 and the insulating layer 60. In one example, the conductive inner layer 28 extends along an inner wall of the extended working channel 18 a distance that is approximately equal to a quarter-wavelength of a desired frequency of the signal being transmitted from the ablation catheter 16.

Upon extension of ablation catheter 16 out of the distal end of the extended working channel 18, contact is made between balun shorts 62 and the conductive inner layer 28 of the extended working channel 18, creating a balun from the combination of the extended working channel 18 and the ablation catheter 16. As will be appreciated, coordination of the location of the conductive inner surface 28 and the location of the balun shorts 62 is required to achieve the desired effect.

In a further embodiment a plurality of balun shorts 62 may be placed along the inner conductor 32 in quarter wavelength increments, resulting in a tunable microwave ablation catheter, whose position may be changed during the course of treatment to achieve a desired tissue effect. As will be appreciated, embodiments where the inner surface 28 of the extended working channel 18 is shorted to the outer conductor 32 of the ablation catheter will require electrical contacts to be placed on the catheter surrounding the ablation catheter and where necessary on the cooling catheters 43 in order to achieve the electrical short.

In an alternative embodiment of the present disclosure, an insulative layer 30 which may be formed of polytetrafluoroethylene (PTFE) may be formed on an internal surface of the conductive inner layer 28 which forms the inner wall of the extended working channel 18. In embodiments, the insulative layer 30 and/or the conductive inner layer 28 may be positioned along the interior of the extended working channel 18 so that the insulative layer 30 and the conductive inner surface 28 in combination with one or more balun shorts 62 form the balun or choke. The internal diameter of the insulative layer 30 may be such that the outer conductor 32 of the coaxial cable 38 passes through the insulative layer in sliding engagement when the ablation catheter 16 is in one of the aforementioned extended configurations. The insulative layer 30 and/or the conductive inner surface 28 and their ultimate orientation with respect to the outer conductor 32 can be adjusted during manufacture to control an overall phase, energy field profile, and/or temperature response of the ablation catheter 16.

As noted above, the ablation catheter 16 may be used in conjunction with the extended working channel 18 in several forms including cooled and uncooled. In one cooled embodiment, the ablation catheter 16 includes one or more columinal cooling catheters 43 which fully encapsulate the distal radiating portion 42. In a second cooled configuration no columinal cooling catheters 43 are used and instead the coaxial cable 38 with radiating portion 42 is simply inserted through the extended working channel 18 and cooling medium is allowed to pass through the extended working channel 18 to cool the radiating portion 42. This embodiment is an open cooling solution and the cooling medium is allowed to escape through the extended working channel 18 into the patient. In a third configuration which permits partial cooling of the coaxial cable 38 up to an insulative layer 30 which is sized to allow sliding engagement of the coaxial cable 38, the radiator 35 of the ablation catheter 16 is not cooled, and any cooling medium directed into the extended working channel 18, may not pass beyond the insulative layer 30, but the remainder of the coaxial cable 38 is cooled. The balun shorts 62, if employed, may be spaced such that they do not significantly impede the flow of the cooling medium. Cooling medium, such as $CO_2$ gas or de-ionized water, may also form part of the balun, providing an additional insulative layer which operates in concert with the conductive layer 28 and the balun short 62 to achieve the desired effect.

Still further, although the microwave ablation catheter 16 described here may be specific, it should be understood to those of skill in the art that other microwave ablation catheter embodiments, either simplified or more complex in structural detail, may be employed without departing from the scope of the instant disclosure.

Figure 4:
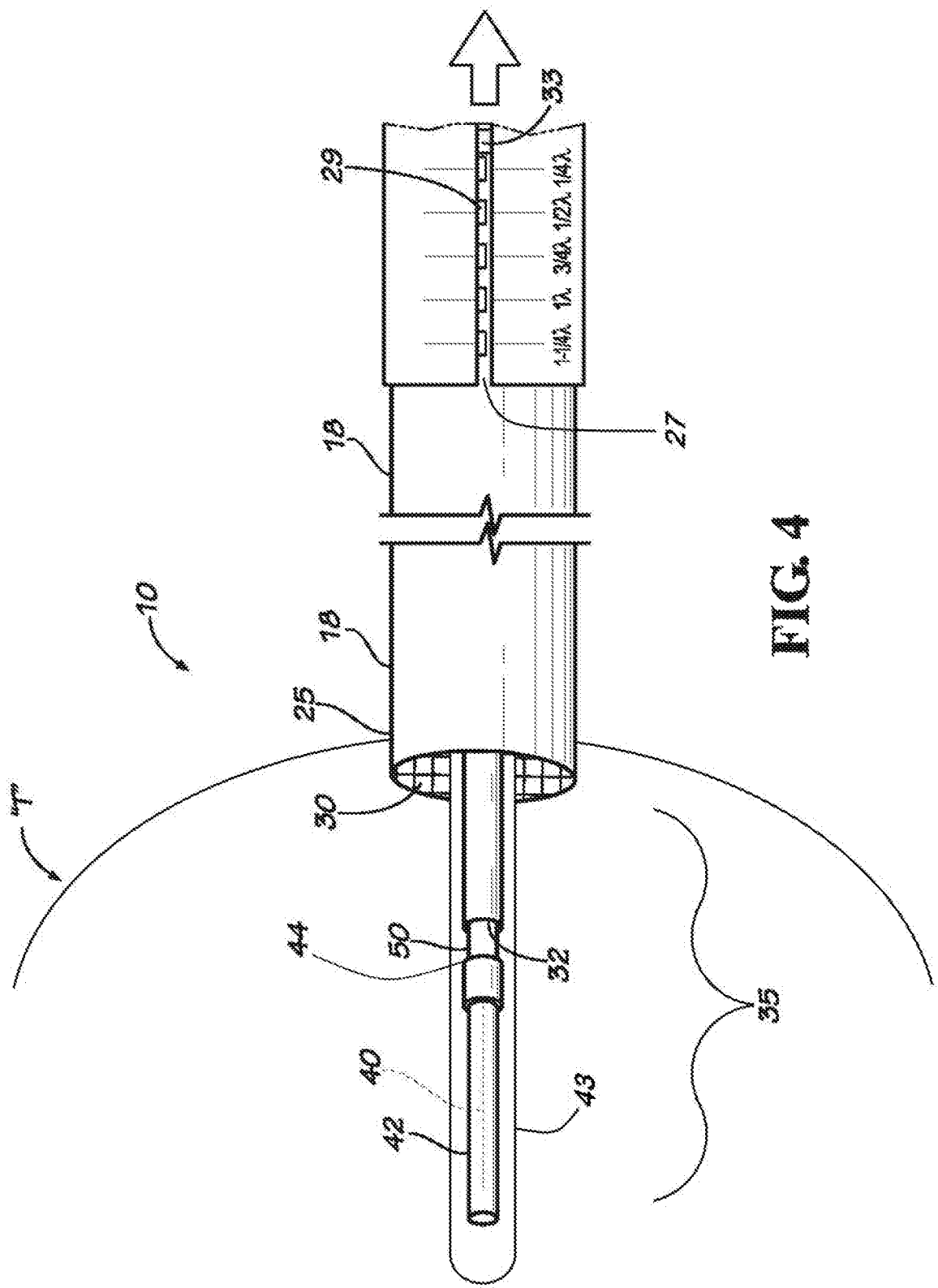
FIG. 4 is a perspective view of the microwave ablation catheter positioned within the extended working channel and with a distal radiating section positioned within target tissue.

Operation of the EMN system 10 to reach an identified target and enable the treatment of target tissue within a lung of a patient is described with reference to FIGS. 1 and 4. As an initial step, imaging of a patient "P" is typically undertaken. For example, CT images may be taken and imported into a pathway planning software. One such pathway planning software is the ILOGIC® Planning suite currently sold by Covidien LP. Typically, in such pathway planning software, the images are viewed and a clinician can identify targets within the images and generate pathways to arrive at the targets. The physician, or user, may use a prior CT scan of the patient "P" and software to construct a representation of the patient's luminal network to help determine and plan pathways to the identified target location. Once the pathway is identified and accepted, this pathway becomes a navigation plan which may be exported to navigation software such as the ILOGIC® Navigation suite currently sold by Covidien LP.

The patient "P" is then placed within the EMN system 10, as depicted in FIG. 1. The location of the patient "P", and particularly features within the luminal structure being navigated (e.g., the lungs) are registered to the images of the navigation plan. Computer system 82, in operation with a tracking module 80, determines the position of the patient "P", and thereby defines a set of reference coordinates, which are matched with the images of the navigation plan. As a result, the navigation software is able to superimpose the location of the sensor 22 onto the images of the navigation plan, and depict to the user the result of the manipulations of the catheter guide assembly 11, 12 on the images of the navigation plan. This system also allows the user to follow the pathway depicted in the navigation plan.

The EMN system 10 utilizes a six degrees-of-freedom electromagnetic position measuring system according to the teachings of U.S. Pat. No. 6,188,355 and published PCT Application Nos. WO 00/10456 and WO 01/67035, the entire contents of which are hereby incorporated by reference. A transmitter arrangement 76 is implemented as a board or mat positioned beneath patient "P." A plurality of reference sensors 78 are interconnected with a tracking module 80 which derives the location of each reference sensor 78 and sensor 22 in 6 degrees of freedom. One or more of the reference sensors 78 (e.g., 3 reference sensors 78) are attached to the chest of patient "P" and their 6 degrees of freedom coordinates are sent to a computer 82 where they are used to calculate the patient coordinate frame of reference.

Once a bronchoscope 72 is inserted into the lungs of a patient "P", the extended working channel 18 and guide catheter assembly 11, 12 including locatable guide 20 and sensor 22 are inserted into the bronchoscope 72. Bronchoscope 72 is connected to monitoring equipment 74, and typically includes a source of illumination and a video imaging system. In certain cases, the locatable guide catheter assembly 12 and extended working channel 18 may be used without a bronchoscope. After advancing the bronchoscope 72 and catheter guide assembly 11, 12, including the extended working channel 18 and the locatable guide 20, to a point of being wedged within a luminal network of the lung, the extended working channel 18 and locatable guide 20 are further advanced along the identified pathway to the target "T". Working in conjunction with the EMN system 10, the guide catheter assembly 11, 12 is used to guide the extended working channel 18 through the luminal network of the patient "P" to the target following the planned pathway relying on the sensed location of the sensor 22 as depicted on the images in the navigation software.

Once at the identified target, the locatable guide 20 may be withdrawn and the extended working channel 18 becomes a pathway to the target "T" for subsequent diagnostic and treatment tools (e.g., biopsy tools, a guide wire, access tools, ablation catheter 16, etc.). Typically, the clinician may seek to take several biopsy samples to confirm that the target "T" is in need of treatment. In some cases, the target tissue may be directly accessed from within the lumen (such as for the treatment of the endobronchial wall for COPD, Asthma, lung cancer, etc.). However, in other instances the target is outside the luminal walls of the bronchial tree and use of the extended working channel 18 and locatable guide 20 alone do not achieve access to the target. Additional access tools may be required to pierce or sever tissue, exit the lumen, and access the target tissue (such as for the treatment of disease within the parenchyma). In embodiments, the target tissue "T" may be pierced or penetrated to allow placement of the radiator 35 of the ablation catheter 16 within the target "T" (e.g., centered within the mass for treatment). For example, a guide wire, piercing tool, a biopsy tool or the distal radiating section 42 of the ablation catheter 16 may be utilized to pierce or penetrate the target "T."

If it is determined that the target "T" requires treatment (e.g., ablation), the ablation catheter 16 may be positioned through the bronchoscope 72 and the extended working channel 18 to enable treatment. Placement of the ablation catheter 16 may occur after the extended working channel 18 has been navigated to the target "T." Alternatively, particularly in embodiments where sensor 22 is incorporated into the extended working channel 18 or into the ablation catheter 16 itself, the mechanical interface 33 of the ablation catheter 16 may be engaged with one of the plurality of mechanical interfaces 29 of the locking mechanism 24 and the extended working channel 18 and ablation catheter 16 may be navigated to the target "T" together. In either case, before energization of the ablation catheter 16, the radiator 35 must be extended to a position distal to the distal end 25 of the extended working channel 18 as the conductive inner surface 28, which beneficially acts as a Faraday cage, as described above, will also substantially prevent radiation from escaping the extended working channel 18 and radiating tissue.

One or more imaging modalities may be utilized to confirm that the ablation catheter 16 has been properly positioned (e.g. within the target "T".) For example, computer tomography (CT), ultrasound, fluoroscopy, and other imaging modalities may be utilized individually or in combination with one another to confirm that the ablation catheter 16 has been properly positioned within the target "T". One methodology employing both CT and fluoroscopy imaging modalities is described in commonly assigned U.S. application Ser. No. 12/056,123 filed on Mar. 26, 2008 by Dorian Averbruch and entitled "CT-Enhanced Fluoroscopy," the entire contents of which are hereby incorporated by reference. Once it is confirmed that the ablation catheter 16 is properly positioned within the target tissue "T," a user may begin with the ablation procedure and apply desired levels of microwave energy to the target "T" to achieve the desired ablation effect.

During the ablation procedure, as the temperature of the target "T" increases, the overall impedance at the tissue site may change, which may lead to an unbalanced signal between the inner and outer conductors 40 and 32. According to one embodiment, to balance the signal, a user can move ablation catheter 16 distally to disengage the mechanical interface 33 of the ablation catheter from the mechanical interface 29 on the extended working channel 18, which moves the distal radiating section 42 further from the outer conductive layer 28. If need be, the user can move mechanical interface 33 into engagement with one of the other mechanical interfaces 29 (e.g., the one that corresponds to a half-wavelength) of the extended working channel 18 to lock the distal radiating section 42 into this further position.

Figure 5:
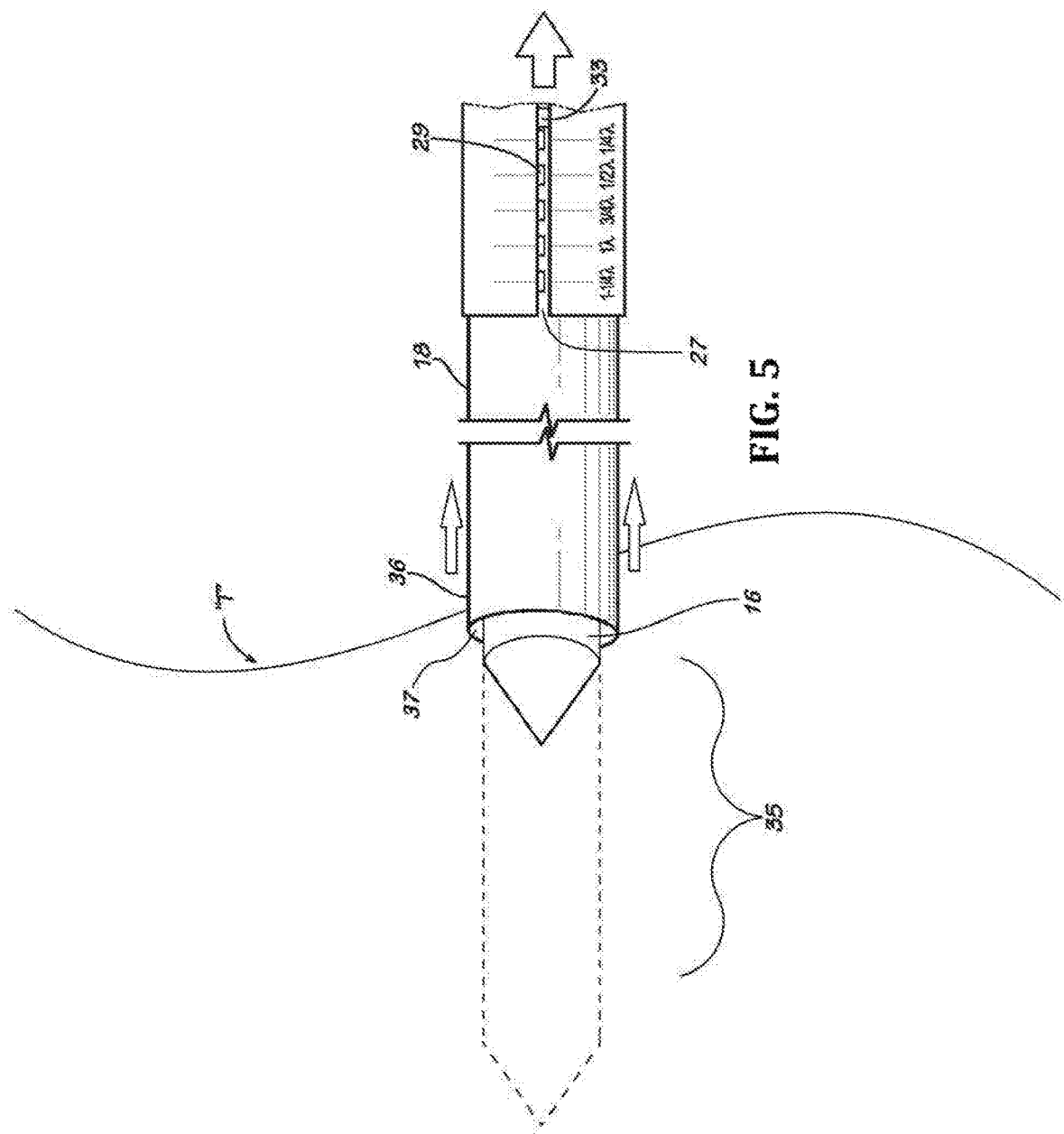
FIG. 5 is a perspective view of the microwave ablation catheter positioned within a metal hypo tube in accordance with the present disclosure.

In yet another alternative embodiment of the present disclosure, the extended working channel 18 may comprise of or may be replaced by a metal hypo tube 36, as depicted in FIG. 5. In this embodiment, the metal hypo tube 36 contains a conductive inner surface 37 and may be optionally coated on its exterior surface with an insulating material as described above with respect to EWC 18. Similar to the conductive inner layer 28 (See FIG. 3A), conductive inner surface 37 functions as an electromagnetic shield for a microwave ablation catheter 16. As described above, the metal hyptotube 36 is configured to receive instruments including the locatable guide catheter 20 and sensor 22, biopsy tools and microwave ablation catheter 16, as well as others without departing from the scope of the present disclosure. During an ablation procedure, metal hypo tube 37, or extended working channel 18 including metal hypo tube 36, is inserted into a patient and positioned adjacent to, or within, target tissue "T." The ablation catheter 16 is then placed within the metal hypo tube 36 and extended past the distal end of the metal hypo tube 36. In one embodiment, the metal hypo tube 36 may be inserted along with an ablation catheter 16 having a pointed or piercing configuration capable of piercing through tissue "T" (as depicted in FIG. 5). Although FIG. 5 depicts ablation catheter 16 with a pointed configuration, the end of the ablation catheter 16 may include any suitable configuration including but not limited to a blunt configuration, flat configuration, hemispherical configuration, bar-bell configuration, tissue piercing configuration, etc. Once the tip of the ablation catheter 16 is placed in the target tissue "T," the metal hypo tube 36 may be retracted to expose radiator 35 of the ablation catheter 16. As explained in greater detail above, the extension of the radiator 35 out of the extended metal hypo tube enables the ablation of tissue, but the length of that extension can be varied as desired to adjust the shape and size of the ablation zone.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave ablation catheter assembly, comprising:
   an ablation catheter including:
   a coaxial cable including an inner conductor and an outer conductor separated by a dielectric; and
   a radiator disposed at a distal portion of the coaxial cable, the radiator including a proximal radiating section and a distal radiating section, the distal radiating section including a conductive element operatively coupled to a distal portion of the inner conductor; and
   a flexible extended working channel configured to receive the ablation catheter for positioning the radiator adjacent target tissue, the flexible extended working channel including:
   an outer insulating layer and an inner insulative layer; and
   a braided electrically conductive inner surface disposed between at least a portion of the outer insulating layer and the inner insulative layer, the braided electrically conductive inner surface electrically shorted to the outer conductor of the coaxial cable,
   wherein the flexible extended working channel is configured such that energy conducted along the outer conductor of the coaxial cable is prevented from affecting tissue adjacent the flexible extended working channel.

2. The microwave ablation catheter assembly according to claim 1, further comprising a location sensor operably coupled to at least one of the ablation catheter or the flexible extended working channel.

3. The microwave ablation catheter assembly according to claim 1, wherein a proximal end of the flexible extended working channel includes a slot configured to releasably engage with a corresponding mechanical interface positioned on the ablation catheter.

4. The microwave ablation catheter assembly according to claim 3, wherein the mechanical interface is moveable within the slot to lock the distal portion of the coaxial cable into at least one of a plurality of positions defined within the slot.

5. The microwave ablation catheter assembly according to claim 4, wherein indicia is provided along the slot in quarter wavelength increments.

6. The microwave ablation catheter assembly according to claim 1, wherein the outer insulating layer is configured to separate the braided electrically conductive inner surface from the tissue adjacent the flexible extended working channel.

7. The microwave ablation catheter assembly according to claim 1, wherein the ablation catheter further includes one or more cooling catheters surrounding the coaxial cable and radiator to provide a pathway for a cooling medium.

8. The microwave ablation catheter assembly according to claim 7, wherein the cooling medium is a liquid or gas.

9. The microwave ablation catheter assembly according to claim 1, wherein the flexible extended working channel provides a closed pathway for a cooling medium to circulate within the flexible extended working channel and around the coaxial cable.

10. A microwave ablation system, comprising:
a microwave energy source;
an ablation catheter configured to operably couple to the microwave energy source, the ablation catheter including:
    a coaxial cable including an inner conductor and an outer conductor separated by a dielectric; and
    a radiator disposed at a distal portion of the coaxial cable and configured to radiate microwave energy generated by the microwave energy source; and
a flexible extended working channel configured to receive the ablation catheter for positioning the radiator adjacent target tissue, the flexible extended working channel including:
    an inner insulative layer; and
    a conductive inner layer disposed around at least a portion of the inner insulative layer and electrically shorted to the outer conductor of the coaxial cable, wherein the flexible extended working channel is configured such that energy conducted along the outer conductor of the coaxial cable is captured within the conductive inner layer of the flexible extended working channel and prevented from affecting tissue adjacent the flexible extended working channel.

11. The microwave ablation system according to claim 10, further comprising a cooling fluid source configured to operably couple to the flexible extended working channel and to supply a cooling fluid for circulation through the flexible extended working channel.

12. The microwave ablation system according to claim 11, wherein the cooling fluid includes at least one of a liquid or a gas.

13. The microwave ablation system according to claim 10, wherein the flexible extended working channel defines at least one fluid delivery channel.

14. The microwave ablation system according to claim 10, further comprising a location sensing system configured to track a location of at least one of the flexible extended working channel or the ablation catheter.

15. The microwave ablation system according to claim 10, wherein a proximal end of the flexible extended working channel includes a slot configured to releasably engage with a corresponding mechanical interface positioned on the ablation catheter.

16. A microwave ablation assembly, comprising:
an ablation device including:
    a coaxial cable including an inner conductor and an outer conductor; and
    a radiator disposed at a distal portion of the coaxial cable; and
an extended working channel configured to receive the ablation device, the extended working channel including:
    an inner insulative layer; and
    an electrically conductive layer disposed around at least a portion of the inner insulative layer and electrically shorted to the outer conductor of the coaxial cable, wherein upon delivery of microwave energy to the ablation device while the ablation device is received within the extended working channel, the flexible extended working channel is configured such that energy conducted along the outer conductor of the coaxial cable is captured within the electrically conductive layer of the extended working channel and prevented from affecting tissue adjacent the extended working channel.

17. The microwave ablation assembly according to claim 16, further comprising a location sensor operably coupled to at least one of the ablation device or the extended working channel.

18. The microwave ablation assembly according to claim 16, wherein a proximal end of the extended working channel includes a slot configured to releasably engage with a corresponding mechanical interface positioned on the ablation device.

19. The microwave ablation assembly according to claim 16, wherein the extended working channel defines at least one fluid delivery channel.

20. The microwave ablation assembly according to claim 16, wherein the extended working channel is flexible.

* * * * *